United States Patent
Le Blanc

(10) Patent No.: US 7,351,956 B2
(45) Date of Patent: Apr. 1, 2008

(54) DYNAMIC BACKGROUND SIGNAL EXCLUSION IN CHROMATOGRAPHY/MASS SPECTROMETRY DATA-DEPENDENT DATA ACQUISITION

(75) Inventor: Yves Le Blanc, Toronto (CA)

(73) Assignees: MDC Inc., Concord (CA); Applera Corporation, Norwalk (*) Notice: Subject to any disclaimer, the term of this patent is extended or adjusted under 35 U.S.C. 154(b) by 227 days.

(21) Appl. No.: 11/334,435

(22) Filed: Jan. 19, 2006

(65) Prior Publication Data

US 2006/0284069 A1    Dec. 21, 2006

Related U.S. Application Data

(63) Continuation-in-part of application No. 10/819,954, filed on Apr. 8, 2004, now Pat. No. 7,009,174.

(51) Int. Cl.
*H01J 49/00* (2006.01)
*B01D 59/44* (2006.01)

(52) U.S. Cl. ............. 250/281; 250/282; 250/288
(58) Field of Classification Search ............. None
See application file for complete search history.

(56) References Cited

U.S. PATENT DOCUMENTS 7,157,700 B2* 1/2007 Kaufman et al. ........... 250/286
2006/0169889 A1* 8/2006 Yokosuka et al. .......... 250/288

* cited by examiner

*Primary Examiner*—Nikita Wells
(74) *Attorney, Agent, or Firm*—Torys LLP

(57) ABSTRACT

Methods and systems for obtaining mass spectrographic data of a substance. Methods include subjecting a substance to a chromatographic process or other separating process, ionizing the output thereof, and subjecting the ionized output to recursive mass spectrometry analyses; and provide improved processing and analysis of data acquired during the repeated analyses. Systems according to one aspect of the invention comprise ion sources, mass spectrometers capable of analyzing ions of selected mass, and controllers adapted to receive from the mass spectrometers and retain signals representing data representing pluralities of mass spectrograms. The controllers can be adapted to generate information useful for describing extracted ion chromatograms, using data associated with the pluralities of mass spectrograms and non-linear curve approximation algorithms; and to use the generated information to generate further information useful in further analysis of the ionized substance.

31 Claims, 12 Drawing Sheets

| Haloperidole Metabolite | m/z | Isomer | Regular-IDA | DBS-IDA |
|---|---|---|---|---|
| CPHP | 212 | 1 | 1 | 1 |
| HP+ | 354 | 1 | 1 | 1 |
| HAL | 376 | 1 | 1 | 1 |
| RHAL | 378 | 1 (2) | 2 | 2 |
| HNO | 392 | 2 | 1 | 2 |
| HAL-Gluc | 552 | 1 | 0 | 1 |
| HAL-Ox-Gluc | 568 | 2 | 0 | 1 |
| Total | | 9 (10) | 6 | 9 |
| % Success | | | 60 | 90 |

FIG. 10a

| Species | m/z | Expected | Regular-IDA | DBS-IDA |
|---|---|---|---|---|
| Diclofenac | 296 | 1 | 0 | 1 |
| 4'-Hydroxydiclofenac | 312 | 1 | 0 | 1 |
| 5-Hydroxydiclofenac | 312 | 1 | 0 | 1 |
| | Total | 3 | 0 | 3 |
| | Success (%) | | 0.0 | 100.0 |

Fig. 10b

DYNAMIC BACKGROUND SIGNAL EXCLUSION IN CHROMATOGRAPHY/MASS SPECTROMETRY DATA-DEPENDENT DATA ACQUISITION

This application is a continuation-in-part of U.S. patent application Ser. No. 10/819,954, filed Apr. 8, 2004 now U.S. Pat. No. 7,009,174 and entitled Dynamic Background Signal Exclusion in Chromatography/Mass Spectrometry Data-Dependent Data Acquisition; and claims the benefit of U.S. provisional patent application 60/461,126, filed Apr. 9, 2003, the entire contents of both of which are incorporated by this reference.

FIELD

The invention generally relates to the field of mass spectrometers and more particularly to automatic MS/MS acquisition using data-dependent acquisition techniques for identifying eluting compounds in a chromatography/mass spectrum system. The invention can also be used for post-acquisition data processing in the identification of a species of interest in a complex mixture.

INTRODUCTION

Mass spectrometers are often coupled with chromatography systems in order to identify and characterize eluting species from a test sample. In such a coupled system, the eluting solvent is ionized and a series of mass spectrograms are obtained of the eluting solvent at specified time intervals, ranging from, for example, 0.01-10 seconds, for subsequent data analysis. As the test sample may contain many species or compounds, it is often desirable to be able to automatically determine or identify species or compounds of interest as they elute and perform MS/MS analysis to characterize them. However, identifying species of interest in complex mixtures in real time can be a challenging task.

A variety of automation tools and data acquisition & analysis software associated with mass spectrometers have been developed to achieve this goal. A well-known automation tool is the Information Dependent Acquisition™ (IDA™) system marketed by MDS Sciex Inc. and Applera Corporation. During the data acquisition process this tool identifies a mass peak in a mass spectrogram so as to select a precursor ion. The tools thus direct one or more subsequent stages of mass spectrometry (MS/MS or MS/MS/MS) in which the chosen precursor ion is fragmented. The resulting MS/MS (or higher) spectrum is a composite of all the fragmentation processes that are energetically allowed: precursor ion to fragment ion and fragment ions to other fragment ions. This spectral richness and/or the dissociation pathways elucidated by subsequent MS stages can be quite useful for identifying compounds when searching through spectral databases or MS/MS libraries or providing structural information used in characterizing compounds.

Vendors of other mass spectrometer systems provide similar real time data-dependent switching functions. For example, Thermo Finnigan LLC of San Jose, Calif., markets the Data Dependent Experiment™ (DDE) tool and Waters Corporation (Micromass™) markets the Data Directed Analysis (DDA) tool.

The above-mentioned real time data dependent switching functions can provide adequate results in applications such as some in-vitro sample analysis or single protein digest analysis where it is possible to a detect a mass peak of interest fairly easily. However, when dealing with a more complex sample set such as a biological fluid, (e.g., urine or plasma extracts) or mixtures of digested proteins (e.g., digested cell lysate), there may be many other major components or species eluting at the same time that will often "shadow" or hide the signal of the analyte or species of interest, which may have weaker signal intensities, thus making it impossible to effectively select the (ionized) species of real interest. In essence, it is often difficult to automatically detect species eluting at a low level of concentration.

In the IDA™ tool, the selection of the mass peak 'chosen' by the system for MS/MS can be improved by relying on a use and inclusion list or by using more specific survey scans such as neutral loss, precursor, and enhanced multiply-charged scans, as known in the art. However, these approaches presume some knowledge of the sample to be analyzed, which is not always the case. Alternatively, a dynamic exclusion process can be activated wherein, once an ion has been selected for dissociation, that ion is ignored over the next few scans such that the ion having the next most significant intensity peak is selected for dissociation. However, this does not solve the problem of weakly-concentrated species that elute simultaneously with a number of other major components.

It will be appreciated that the proper selection of precursor ions is an important step in species identification. The proper selection of ions will also ensure that a useful yet minimal amount of information is collected in data-dependent acquisition techniques, which can assist in speeding up and simplifying species identification and characterization.

SUMMARY

Generally speaking, systems and methods according to the invention are able to identify weakly-concentrated and other species that elute simultaneously with a number of other major components by identifying ions having fast-rising or otherwise distinctive mass signals. This is preferably carried out by comparing a mass spectrum(s) against a spectrographic background which may comprise one or more previously acquired mass spectrums.

According to one aspect of the invention, a method of obtaining mass spectrographic data of a substance is provided. In the method, a substance is subjected to a chromatographic process and the output thereof is ionized. A mass spectrogram is obtained of the ionized output. The ion (or ions) having the fastest rising mass signal(s) is/are then identified by comparing the current mass spectrum against a spectrographic background which may comprise one or more previously acquired mass spectrums of the output. The identified ion(s) may then be fragmented and a resulting mass spectrum recorded. These steps are preferably dynamically repeated so that substantially all eluting species from the chromatographic column are identified by mass and fragmented to obtain additional mass spectral information.

Ions associated with fast-rising mass signals may be identified by, for example, subtracting one, or an average of, previously acquired mass spectrums from the current mass spectrum. Alternatively, ion(s) associated with fast-rising mass signals may be identified by determining a percentage change in the value of each mass signal in a current mass spectrum against its value or average value in one more of the previously acquired mass spectrums of the output.

Identification of fast-rising mass signals may be refined or otherwise improved through the application of further mathematical techniques, including for example various data- or curve-smoothing or approximation algorithms, and/or further algorithms adapted to, for example, approximate rates of increase or decrease or other derivatives describing the elution of various analytes using mathematically-deduced or -approximated curve forms. For example, in an LC/MS/MS analysis one or more ions having mass-charge (m/z) ratios of interest may be identified, and respective whole or partial extracted ion chromatograms (XICs) may be generated, based on the intensity of those ion(s) over a number of previous MS scans, by accessing data representing ion current at specific points in time associated with the previous scans and applying curve-fitting or other curve approximation algorithms to the data. First or other derivatives (with respect, for example, to time) at points of interest in time can be determined, or approximated, to determine whether the rate(s) of elution for the ion(s) is fast-rising or otherwise of interest.

Thus in another aspect the invention provides systems for and methods of obtaining mass spectrographic data describing substances. Systems according this aspect comprise ion sources, mass spectrometers capable of analyzing ions of selected mass, and controllers adapted to receive from the mass spectrometers and retain signals representing data representing pluralities of mass spectrograms. The controllers can be adapted to generate information useful for describing extracted ion chromatograms, using data associated with the pluralities of mass spectrograms and non-linear or other curve approximation algorithms; and to use the generated information to generate further mass spectral information useful in further analysis of the ionized substance (for example, but not limited to MS/MS spectra).

The invention further provides methods suitable for implementation using such systems.

If desired, one or more identified ions may be placed on a dynamic exclusion list. Such ions will thereafter not be considered as being associated with the fastest-rising mass signal, or otherwise of interest, thereby enabling the identification and selection of one or more ions associated with other fast-rising signals for subsequent mass analysis. If desired, a precursor or neutral loss scan may also be conducted prior to identifying the ion having a fastest rising mass signal.

Other schemes and processes may be used to reduce the amount of data recorded and subsequently processed by the mass spectrometer and its controller(s), and to thereby speed or otherwise increase the efficiency and accuracy of the analysis process. For example, one or more thresholds may be established, so that data is recorded and further processed only for ions of m/z ratios detected by the mass spectrometer at least at a desired minimum intensity rate, or prior to determining a detected intensity rate. This can help, for example, in reducing the processing of data related to impurities or substances otherwise not of interest, and can be particularly effective when used in conjunction with other methods and processes according to the invention.

Once the mass spectrographic data has been acquired, mass spectrum(s) obtained from, for example, the fragmentation of identified ion(s) can be compared against a database of mass spectrums in order to automatically identify an eluting compound, or otherwise used for compound characterization.

In other aspects the invention provides systems and apparatus for carrying out the foregoing methods and processes.

BRIEF DESCRIPTION OF DRAWINGS

The foregoing and other aspects of the invention will become more apparent from the following description of specific embodiments thereof and the accompanying drawings which illustrate, by way of example only and not intending to be limiting, the principles of the invention. In the drawings:

FIG. 10, including parts 10a and 10b, provides tables of comparative results obtained using processes according to prior art and processes according the invention.

DESCRIPTION OF VARIOUS EMBODIMENTS

Figure 1:
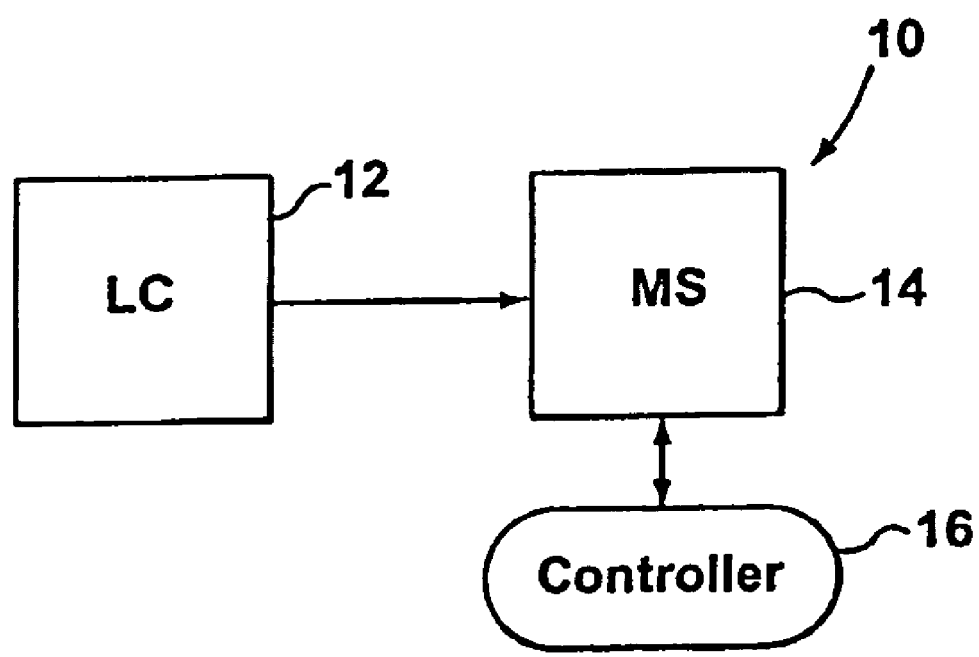
FIG. 1 is a schematic block diagram of an LC/MS system suitable for use in implementing the invention.

FIG. 1 shows basic components of a liquid chromatography-mass spectrometry (LCMS) system 10 which includes a chromatography column 12 coupled as known in the art to a mass spectrometer 14 capable of conducting multiple stages of mass spectrometry. An example of such a system is the QSTAR™ or API 4000™ LC/MS/MS system marketed by MDS Sciex, although those skilled in the art will appreciate that the invention can be applied to any suitably-controlled system that has MS and MS/MS or other multi-MS capabilities (e.g., a 3D trap, time-of-flight (TOF) analyzer, or Fourier Transform (FTMS) analyzer). Data acquisition controller 16 enables automated MS to MS/MS data acquisition for maximum extraction of information from a single LC/MS analysis.

Controller 16 is adapted for receiving, storing, and otherwise processing data signals acquired or otherwise provided by mass spectrometer 14, and for providing command signals adapted for the control of operations performed by mass spectrometer 14. Controller 16 further provides a user interface suitable for controlling the MS system 10, including for example input/output devices suitable for accepting from the user and implementing system commands. In particular, controller 16 is adapted for processing data acquired by mass spectrometer 14 and providing to mass spectrometer 14 command signals determined at least in part on information generated by the processing of such data.

As will be understood by those skilled in the relevant arts, controller 16 can comprise any data-acquisition and processing system(s) or device(s) suitable for accomplishing the purposes described herein. Controller 16 can comprise, for example, a suitably-programmed or -programmable general- or special-purpose computer, or other automatic data processing equipment, with associated programming and data acquisition and control devices. Controller 16 can be adapted, for example, for controlling and monitoring ion detection scans conducted by mass spectrometer 14; and for acquiring and processing data representing such detections by mass spectrometer 14 of ions provided by, for example, liquid chromatography (LC) column 12, as described herein.

Accordingly, controller 16 can comprise one or more automatic data processing chips adapted for automatic and/or interactive control by appropriately-coded structured programming, including one or more application and operating system programs, and any necessary or desirable volatile or persistent storage media. As will be understood by those of ordinary skill in the relevant arts, once they have been made familiar with this disclosure, a wide variety of processors and programming languages suitable for implementing the invention are now available commercially, and will doubtless hereafter be developed. Examples of suitable controllers, comprising suitable processors and programming are those incorporated in the QSTAR™ or API 4000™ LC/MS/MS systems available through MDS Sciex of Ontario, Canada.

Ion sources suitable for use in implementing the invention can comprise any LC column or other ion source 12 compatible with the purposes disclosed herein. For example, as will be apparent to those skilled in the relevant arts, any liquid chromatography or other sustained-release ion sources will serve. The invention is particularly useful in combination with LC columns and other ion sources that produce sustained or other streams of ions of varying character, including for example LC-Matrix-Assisted Laser Desorption Ionization (LC-MALDI) systems adapted for continuous trace deposition.

Mass spectrometer 14 can comprise any ion detector and/or analyzer compatible with the purposes disclosed herein. For example, as will be apparent to those skilled in the relevant arts, 3D ion traps, TOF detectors, and other types of mass spectrometers will serve. The invention is particularly useful in combination with mass spectrometers capable of repeated or recursive scans or other samplings of ion groups.

Figure 2:
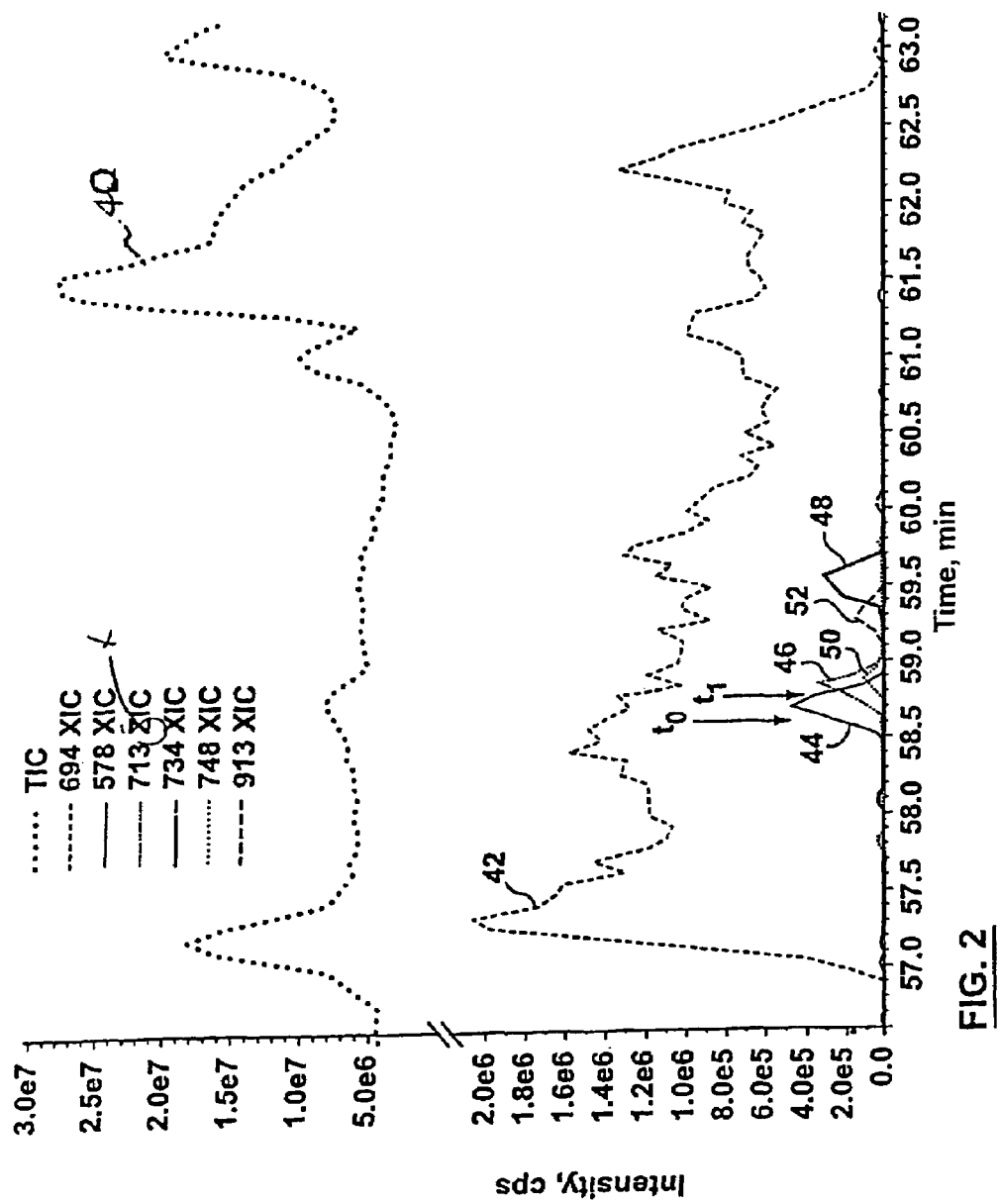
FIG. 2 is a graph which plots the intensity (cps) of various masses detected as function of time (minutes) over a portion of an LC/MS run.

FIG. 2 shows a portion of the data output as part of an LC/MS analysis carried out on human growth hormone (Hgh) digest using an API3000™ system. The data shown pertains to the $57^{th}$ to $63^{rd}$ minutes of the analysis run. Signal 40 plots the total ion intensity (TCI) of the run, which represents the total concentration of all eluting species. The mass spectrometer 14 also records the ion intensity for a predetermined range of masses (more specifically, m/z range) and signals 42 to 52 plot extracted ion counts for ions of mass-to-charge ratios of 694 m/z, 578 m/z, 713 m/z, 734 m/z, 748 m/z and 913 m/z, respectively. These signals chart the intensities of various (but not all) eluting species over this time period.

Figure 3:
FIG. 3 is a mass spectrogram taken at a first time ($t_1$) in the portion of the LC/MS run shown in FIG. 2.
Figure 4:
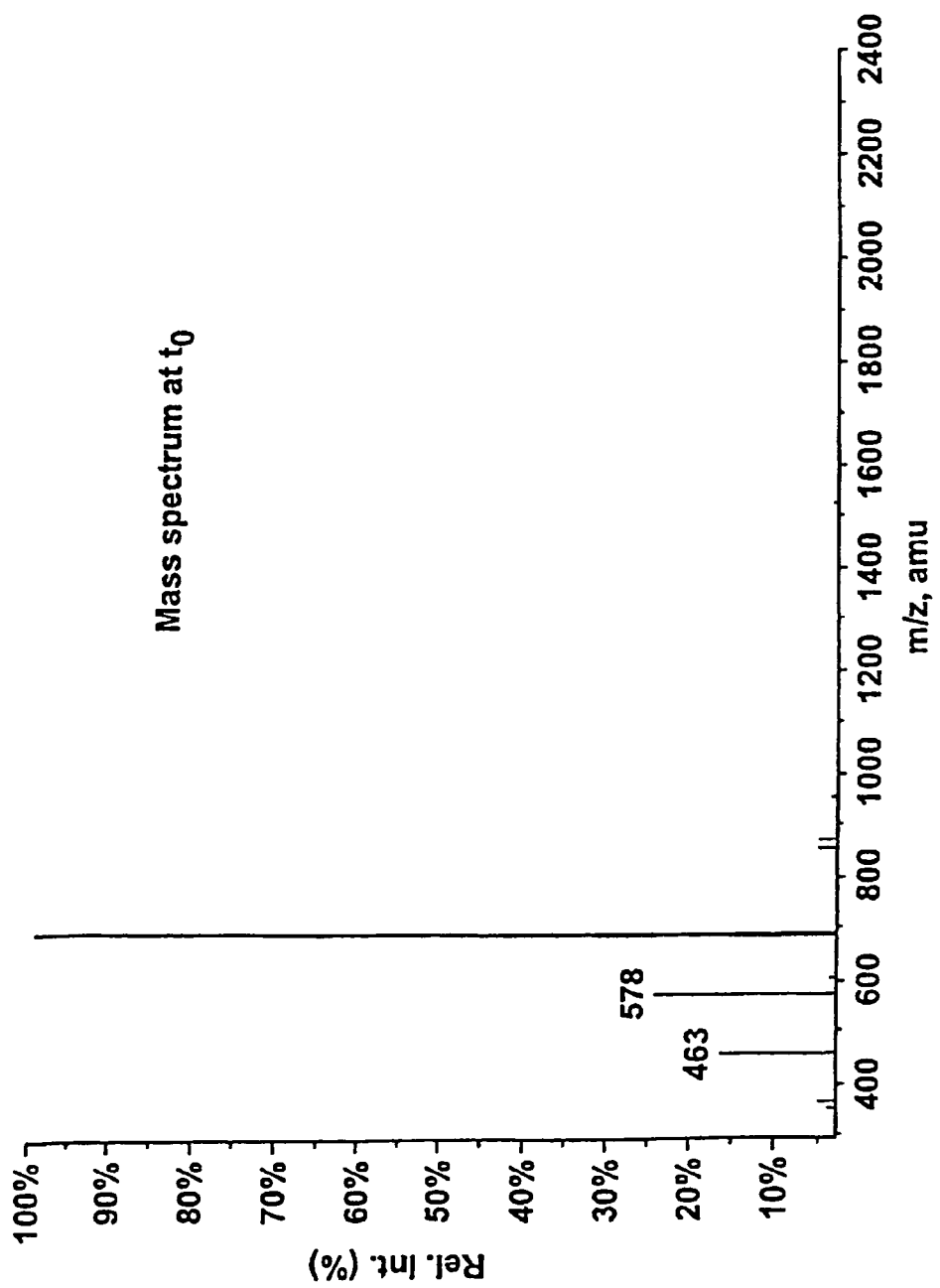
FIG. 4 is a mass spectrogram taken at a second time ($t_o$) in the portion of the LC/MS run shown in FIG. 2.

It may be seen that between approximately 58.5 to 59 minutes of the run, there are a number of eluting species, a subset of which are shown in FIG. 2. The MS spectrograms for these eluting species obtained at times $t_0$ and $t_1$ are shown in FIG. 3 (time $t_1$) and FIG. 4 (time $t_0$), and the ion intensities at each of these instances of time are tabulated in table 1 below.

Since a number of mass peaks appear in the spectra at about the same time, prior art systems have a difficult time selecting a mass peak on which to conduct a secondary mass analysis. The problem is further exacerbated because a number of low intensity signals (in particular ions of mass 578 m/z, 713 m/z, and 748 m/z) exist in the presence of a high intensity signal generated by ion 694 m/z.

Figure 5:
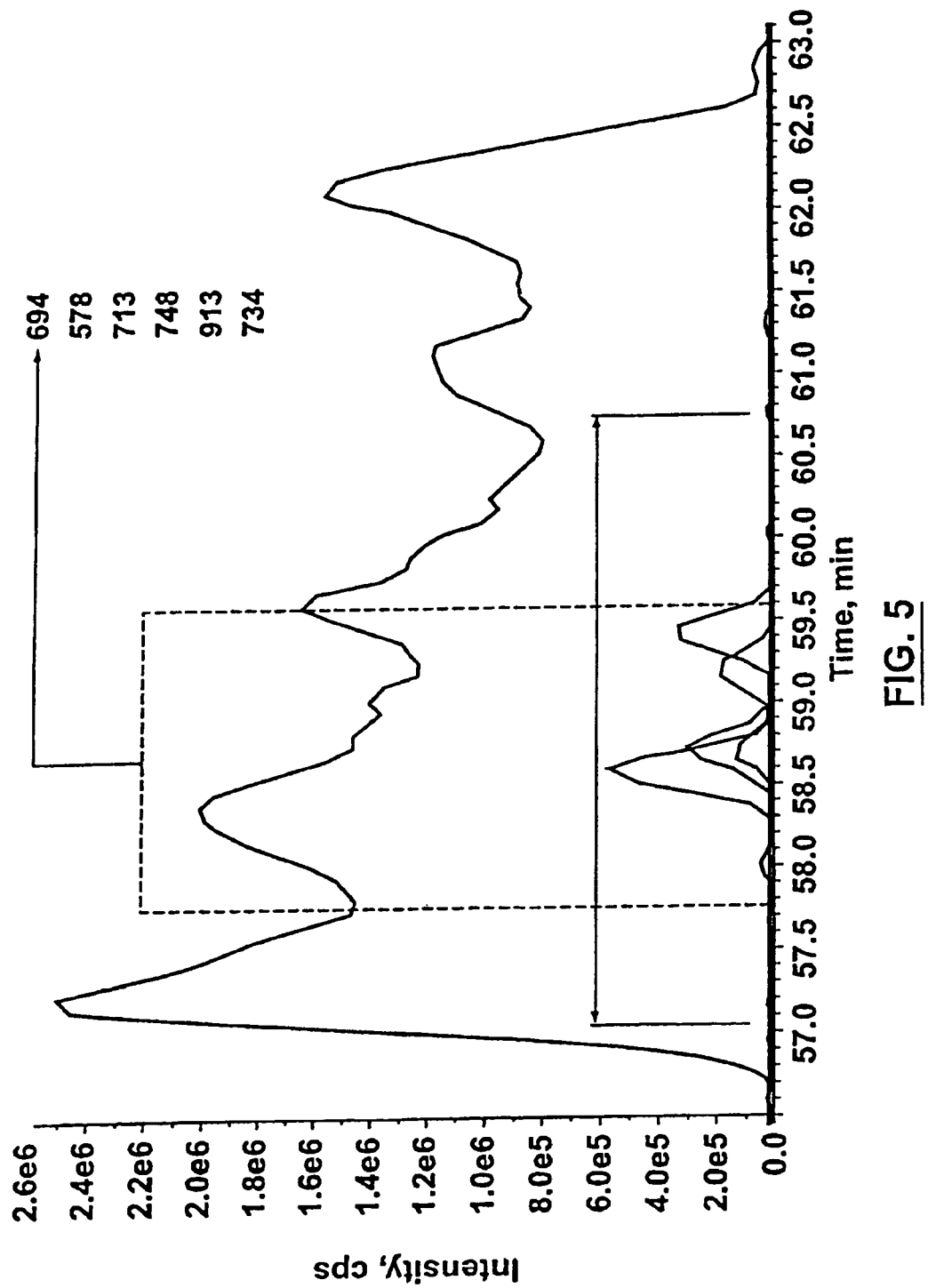
FIG. 5 is a schematic diagram illustrating ions(s) that would have been selected for a secondary mass analysis using a data-dependent acquisition tool of the prior art, without Dynamic Background Signal Exclusion according to the invention.

FIG. 5 is a schematic diagram illustrating the ions(s) that would have been selected by prior-art controllers for secondary mass analysis using a data-dependent acquisition tool of the prior art, without Dynamic Background Signal Exclusion according to the invention. FIG. 5 shows that between 57.16 and 60.76 minutes of the run, the prior art data acquisition controller (the IDA™ system) would have selected only ion 694 m/z for conducting a secondary mass analysis (when the system is not programmed to apply dynamic exclusion criterion). However, other masses with chromatographic behavior eluted during that time, representative masses that eluted over the shaded area being shown in the Figure. Thus the quality of the analysis would have been adversely affected by use of prior art systems.

In contrast, in the preferred embodiment controller 16 attempts to identify the fastest-rising or other fast-rising signals at any given point in time by comparing the most recently-acquired MS spectrogram(s) against a dynamic "spectrographic background". For ease of illustration, a simple example of this technique can be understood by comparing FIG. 3 (which is later in time) against FIG. 4 (which is earlier in time). From this comparison it will be seen that mass 748 m/z has the fastest rising signal (which corresponds to signal 50 in FIG. 2).

This phenomenon can be quantified by controller 16 using two simple quantification methods: (i) a subtraction of the current value of the signal against its value in a previously acquired MS spectrogram; and (ii) a percentage change in the value of the signal. Table 1 shows that by using either of these criterion, controller 16 will move ions of both 748 m/z and 713 to the top of the list for the IDA selection.

TABLE 1

| | | | | | IDA Order of Selection | |
|---|---|---|---|---|---|---|
| m/z | $t_0$ | $t_1$ | Subtraction | Percentage change | Most Intense (prior art) | Background Subt. (preferred embodiment) |
| 578 | 7.33e5 | 7.10e5 | −2.25e4 | −0.03 | 2 | Not selected |
| 694 | 2.95e6 | 2.66e6 | −2.93e5 | −0.10 | 1 | Not selected |
| 713 | 5.00e4 | 1.20e5 | 1.20e5 | 1.40 | 4 | 2 |
| 748 | 5.00e4 | 3.20e5 | 3.20e5 | 5.40 | 3 | 1 |

Having thus selected ions of mass 748 m/z and 713 m/z, controller 16 can provide to mass spectrometer 14 command signals adapted to dynamically operate the spectrometer 14 to carry out a secondary mass analysis by fragmenting these ions and recording the resulting mass spectrum. In the preferred embodiment, a predetermined number of selected ions are fragmented but in alternative embodiments only the "best" match, e.g., ion 748 m/z, may be selected for subsequent fragmentation.

Both quantification methods described above offer advantages: in many circumstances the percentage or relative gain is the preferred technique when the focus is on rate of growth, whereas the absolute gain calculated by the subtraction method concentrates on species that have a significant increase. The term "fast-rising signal" is specifically defined to include a signal rising quickly in relative terms, i.e., calculated by the rate of growth, or in absolute terms, i.e., calculated by the subtraction method.

Figure 6:
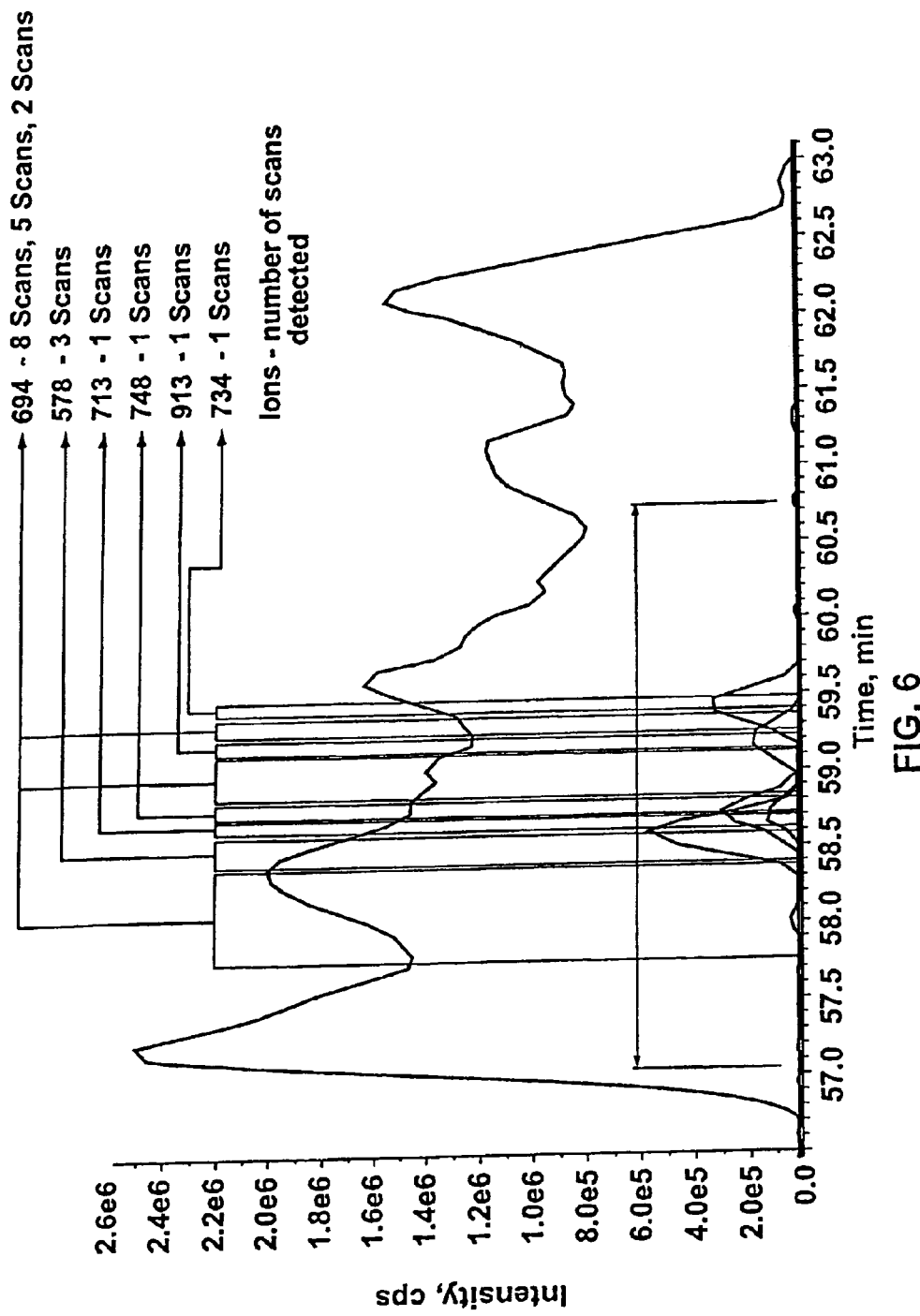
FIG. 6 is a schematic diagram illustrating ions selected for a secondary mass analysis in accordance with a preferred embodiment of the invention.

FIG. 6 illustrates the results of these techniques on data obtained between the 57.16$^{th}$ and 60.76$^{th}$ minutes of the run. Each block 60 represents one or more sequential scans where a different ion mass peak is selected by the controller 16 for conducting a secondary MS analysis. The value of the selected m/z ratio and the respective number of scans (e.g. 694-8 scans, 5 scans, 2 scans) for which the identified m/z range was selected is indicated. Thus FIG. 6 is a schematic diagram illustrating ions selected for a secondary mass analysis in accordance with an embodiment of the invention which attempts to identify the fastest rising mass signal at any given point in time. With Dynamic Background Signal Exclusion, more ions were successfully selected for IDA, even when they were not the base peak of the mass spectrum. If the ions correspond to a signal rising faster than a signal corresponding to other selected ions, they are detected and the data used for further analysis.

Figure 7:
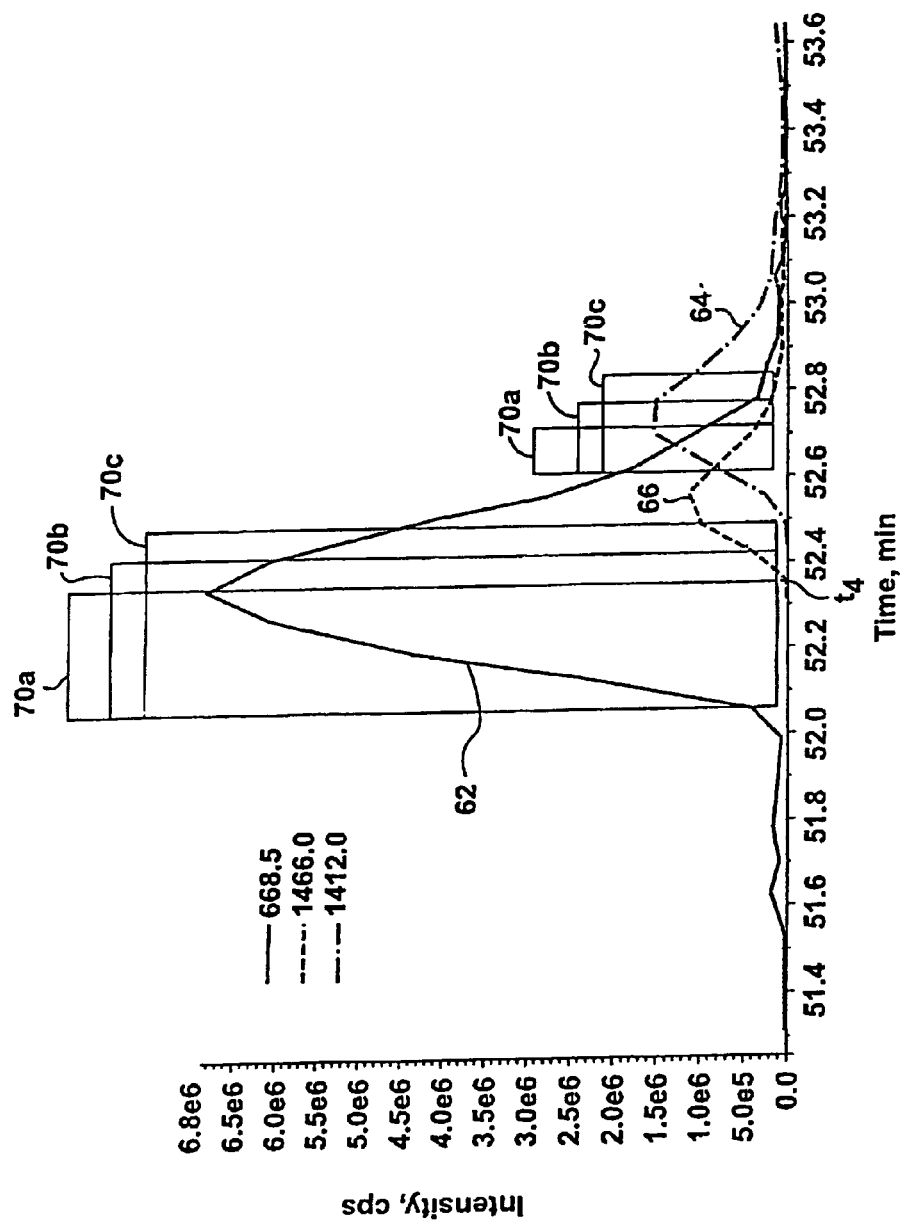
FIG. 7 is a schematic diagram illustrating portions of a mass peak which may be considered in the detection of a fast-rising mass signal.

In the example presented thus far controller 16 accessed data representing one immediately-preceding MS spectrogram to determine the spectrographic background. However, it is possible in the alternative for controller 16 to average a mass signal over a number of MS spectrograms in order to obtain the spectrographic background for comparison purposes. For example, FIG. 7 shows various extracted ion counts obtained during minutes 51.4 to 53.6 of the LC/MS run for ions of mass 668.5 m/z, 1412.0 m/z and 1466.0 m/z, as respectively shown by signals 62, 64 and 66. As indicated by the blocks 70a, 70b, and 70c in FIG. 7, the number of spectra used to determine the average background value of a signal determines the scope of coverage or the number of data points that will be selected across a mass peak. For example, in block 70a the background average value for signal 62 at time $t_4$ is obtained from one immediately preceding spectrogram (obtained 0.05 minute, or 3 seconds, prior) and hence the controller considers only the rise in the signal. As soon as the signal passes its peak value, the result is a negative number using either a subtraction or percentage change basis, as will be noted by subtracting the value of signal 62 at time $t_4$ from its value at time $t_3$.

However, in block 70b results are shown when controller 16 accesses data representing three immediately-preceding spectra in order to determine the background value of signal 62, resulting in a greater scope of coverage or number of data points considered across a mass peak. Block 70c indicates the scope of coverage when ten preceding spectra are employed to determine the background value of the signal 62. Such techniques, similar to moving averages, assist in smoothing out sudden perturbations in the signals and hence spurious results. The number of spectra the controller uses to determine the average background value of a mass signal may preferably be set or overridden by a user of the system.

An especially advantageous manner of using data available from a number of MS spectrograms generated by, for example, a repeated or recursive MS cycle in smoothing out sudden perturbations in the signals and reducing spurious results is through the application of further mathematical techniques, including for example various data- or curve-smoothing algorithms used to evaluate rates of increase or decrease or other aspects of the elution of various analytes from an ion source such as an LC column. As noted, the number of spectrums controller 16 uses to determine the average background value of a mass signal may be set or overridden by a user of the system, or may be determined automatically by the system based, for example, on statistical assessments of data quality.

For example, in an LC-MS analysis controller 16 can identify one or more ions having mass-charge (m/z) ratios of particular interest, and generate respective whole or partial XICs generated, based on the intensity of identified ion(s) detected by mass spectrometer 14 over a number of previous MS scans. This may be done, for example, by accessing data representing one or more ion current(s) at specific points in time associated with a designated number of previous scans, and applying curve-fitting or other suitable algorithms to the data. First or higher-order derivatives (with respect to time, for example) at various temporal or other points of interest in the analysis, based on smoothed or otherwise approximated or estimated data curves, may be determined in order to determine whether, for example, the rate(s) of elution for the ion(s) is fast-rising or otherwise of interest for further analysis. Such techniques are particularly useful in, for example, identifying fast-rising signals by calculating a rate of growth, etc.

The value of such techniques in the rapid and accurate assessment of the status or content of eluted or otherwise-provided ions may be enhanced through the additional use of any one or more additional processes for concentrating analysis on desired portions of detected mass spectrums.

For example, in some embodiments of the invention selection of ions for secondary MS analysis may be based on other criterion in addition to or in combination with the criterion of a fastest rising mass signal. For example, if desired, the dynamic background comparison described above may be combined with dynamic exclusion. For example, in one scheme, an ion identified as associated with a fast-rising mass signal can be placed on an exclusion list and not considered for a predetermined number of subsequent MS scans. This technique can be further augmented by delaying the placement of an ion on the exclusion list until after that ion has been selected a pre-determined number of consecutive times as an ion having a fastest rising mass signal. In addition, if desired, the controller may employ MS or MS/MS scans (e.g., precursor and/or neutral loss scans) prior to the application of the dynamic background comparison.

As another example, one or more thresholds may be established automatically, and/or interactively by a user, and used by the controller 16 as a criterion in determining which data acquired in a given scan or series of scans should be stored or otherwise retained for further processing, so that data is recorded and further processed only for ions of m/z ratios detected by the mass spectrometer at a desired minimum intensity rate.

As indicated, data curve smoothing algorithms, dynamic exclusion techniques, intensity thresholds, and other techniques can be used to improve data processing efficiency by, for example, reducing the processing of data related to impurities or substances otherwise not of interest collected and subsequently processed by controller 16. Such techniques can be particularly effective when used in conjunction with each other, and/or with other methods and processes according to the invention. They are particularly useful where high data scanning/collection rates are encountered, as for example in recursive TOFMS and/or FTMS analyses.

Figure 8:
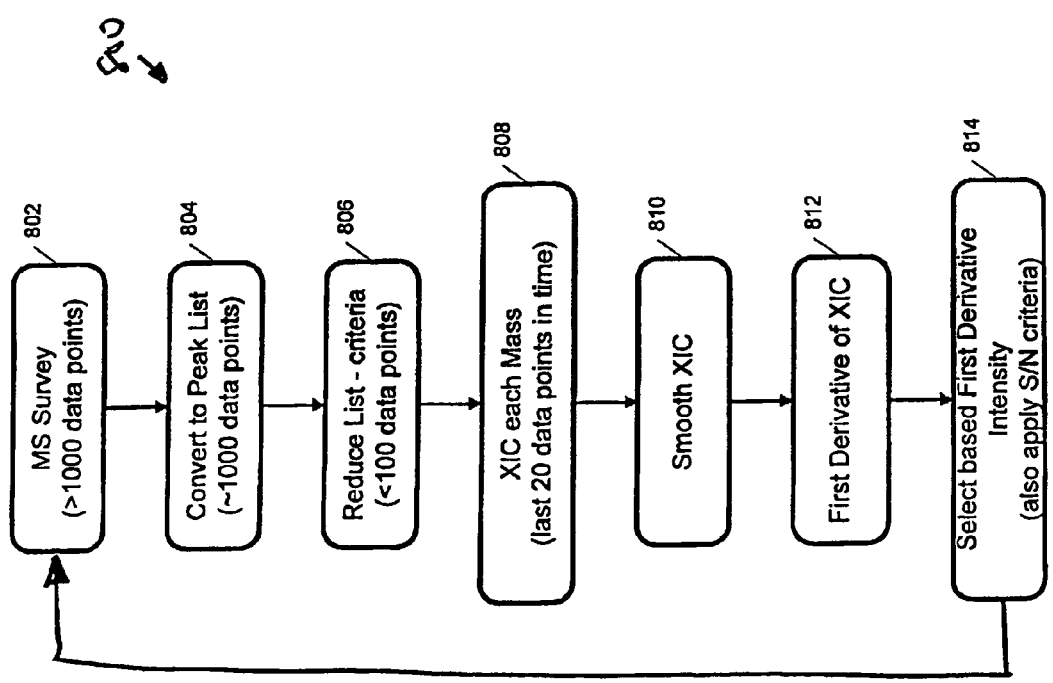
FIG. 8 is a schematic diagram illustrating a method for processing data recorded in a multi-MS analysis in accordance with the invention.

FIG. 8 is a schematic diagram of an embodiment of a method for processing data recorded in a recursive TOFMS analysis in accordance with the invention. Process 800 is suitable for implementation by, for example, a system such as that shown in FIG. 1, under the control of a controller such as controller 16.

At 802 controller 16 issues command signals adapted to cause mass spectrometer 14 to perform a survey scan of a detector associated with the mass spectrometer, and provide to the controller 16 data representing m/z ratios associated with ions detected by the detector. In the case for example of a TOF mass analyzer, mass spectrometer 14 can provide to controller 16 data representing a number of m/z ratios associated with ions detected by the detector within a given time span or during a given survey period, preferably in conjunction with the time (such as a relative time elapsed since the beginning of the current survey period) at which the respective ions were detected. In some cases, the amount of data acquired during the scan by spectrometer 14 and provided to controller 16 can be relatively large. For example, in the case of a typical analysis conducted by a QSTAR™ LC/MS/MS system, a complete survey of the detector during the scanning time period can result in the acquisition by the detector of many thousands of data points (e.g., on the order of 10,000 to more than one million, with 500,000 being a typical number), each consisting of a relative time and an m/z intensity which corresponds to the number of ions detected. Controller 16 can hold the acquired data in volatile memory, as for example a random access or flash memory, or other readily-available buffer.

At 804, controller 16 can sort the data provided by mass spectrometer into a peak list, as for example by determining a total number of ions of each m/z ratio detected during the survey scan at 802, and preferably retaining data related to m/z ratios of interest while ignoring or deleting the rest. Controller 16 can advantageously continue to hold the sorted data, which may now be referred to as a peak list, in volatile or other ready-access memory. The sorted data can correspond, to example, to a trace such as that corresponding to the scan initiated at a time $t_1$ and shown in FIG. 3. In the case of a typical analysis conducted by a QSTAR™ LC/MS/MS system, this can result in the number of data points of interest associated with a given survey of the detector being reduced from the 10,000 to more than one million data points acquired during the complete survey to something on a considerably smaller order, as for example something like 1000 data points in a typical analysis. The reduced data set may be maintained in volatile memory and/or stored in persistent memory for future access and processing.

Ions and/or m/z ratios included at 804 in the retained data identified by the peak list can, as described herein, be identified automatically by controller 16, using processes described herein, or can be designated by a user of the system 10 by means of, for example, batch or interactive instruction signals provided to the controller 16.

At 806, controller 16 can reduce the data held required to be held in volatile memory, or otherwise subsequently processed by controller 16, by applying data reduction techniques such as those described herein. For example, controller 16 can compare the intensities (e.g. total detected ions) of data representing various m/z values (or peaks) detected during a given scanning survey to a threshold established by a user or otherwise determined by the system 10. For example, an absolute or relative intensity threshold of a given charge or detection level can be established, and controller 16 can be instructed, as for example by suitable programming, to ignore m/z values corresponding to peaks of intensities below the established threshold value. For example, a threshold of 5.0e5 cps can be established, so that data corresponding to m/z ratios of a detected charge intensity below that threshold would not be retained or considered for further processing. This would result, for example, in the data corresponding to peaks 901 of FIG. 9, being dropped from further consideration so that the peaks 901 would not appear in the cumulative trace of FIG. 9, and only data associated with curves or peaks 62, 64, 66 would be further processed.

Alternatively, or in addition, a relative value can be established. For example, in the analyzes corresponding to the traces shown in FIGS. 3 and/or 4, peaks of a relative intensity lower than a selected threshold can be dropped from further processing. If for example a threshold of 10% is set, controller 16 can stop processing of data related to peaks 371, 1121, 1530, 713, and 887, and others shown in FIG. 3 but not labeled.

As a further example, at 806 controller 16 can reduce the data held in volatile memory, or otherwise subsequently processed by controller 16, by applying ion exclusion criteria as described herein, so that data corresponding to selected m/z ratios is dropped from further processing by controller 16.

Applications of such data reduction techniques at 806 can result, in the case of a typical analysis conducted by a QSTAR™ LC/MS/MS system, in a reduction of the number of data points of interest associated with a given survey being reduced from the 1,000 or so points retained following step 806 to something like 100 data points (or lower), each representing an m/z ratio of interest and an intensity of charge recorded during the respective survey or scan period. The reduced data set may be maintained in volatile memory and is preferably stored in persistent memory for subsequent access and processing. As will be apparent to those of ordinary skill in the relevant arts, the substantial decrease in the amount of processed data can result in vastly increased processing times for data of interest, thus increasing both the number and quality of outputs that may be generated related to the data and increasing the rate at which MS scans can be processed, which can as discussed herein improve the quality of data acquired and processed by the system 10.

At 808 controller 16 can access data associated with a selected number of previous survey scans and generate an XIC for one or more designated ions (i.e. m/z ratios) of interest. This can be accomplished in a wide variety of ways. For example, as a first step a first-order curve approximated by line segments represented by straight lines drawn between individual time-m/z intensity data points (sometimes referred to as mass-intensity pairs) may be generated. Such a curve is illustrated by curve 62 in FIG. 9, which consists of straight line segments drawn between data points 62-1 through 62-22. Data associated with an XIC generated in this manner can be used, for example, to identify fast-rising signals as described herein.

It is sometimes observed, however, that the use of first-order (i.e., linear) curve approximations generated by straight-line connections between data points in XICs can lead to inaccuracies or other difficulties in analysis. For example, where the relative proportions of the constituent components of an analyzed sample eluted or otherwise provided by an ion source 12 change at rates that are relatively high, when compared to cycle times between MS survey scans, peaks and valleys in the rates of elution or provision can be missed and consequently under-estimated, resulting in the misidentification of compounds and/or relative levels of constituents thereof. Similarly, when rates of contact by ions of various m/z ratios strike regions of detector plates in mass analyzers 14 are too high to be processed completely by the analyzers (i.e. when the processing capacity of regions of the detectors are exceeded, or the detectors are saturated), peaks in XIC traces can be under-estimated, with similar results.

Thus in many instances the quality of spectrographic analysis can be improved through the use of improved second- or higher-order, or other non-linear (or even improved linear) curve representations based on series of acquired data points. Thus at 810 controller 16 can access acquired trace data and perform any of a variety of XIC curve-smoothing algorithms to provide curve approximations for all or any portions of XICs generated by the controller 16. Algorithms performed by controller 16 can include any suitable curve-fitting or smoothing algorithms, or other suitable mathematical operations, including for example varied linear and nonlinear curve-fitting methods, including least squares, weighted least squares, and robust fitting (all with or without bounds); splines and interpolations including polynomials of degree 2 or higher and exponential functions; and can be used to determine a wide variety of information concerning the generated XICs, including for example local or complete XIC curve approximations; rates of change at any one or more points on the curves (first derivative), local minimum and maximum points of the curves (zeros of the first derivative), and the area under the curve (integral).

Algorithms suitable for any of the purposes disclosed or suggested herein may be used. As will be appreciated by those skilled in the relevant arts, once they have been made familiar with this disclosure, a large number of suitable algorithms are known, and will doubtless hereafter be developed. In one embodiment, a first derivative is used with simple non-linear smoothing of 2-3 points per data point pair in order to compare intensity derivatives for dynamic ion selection.

Figure 9:
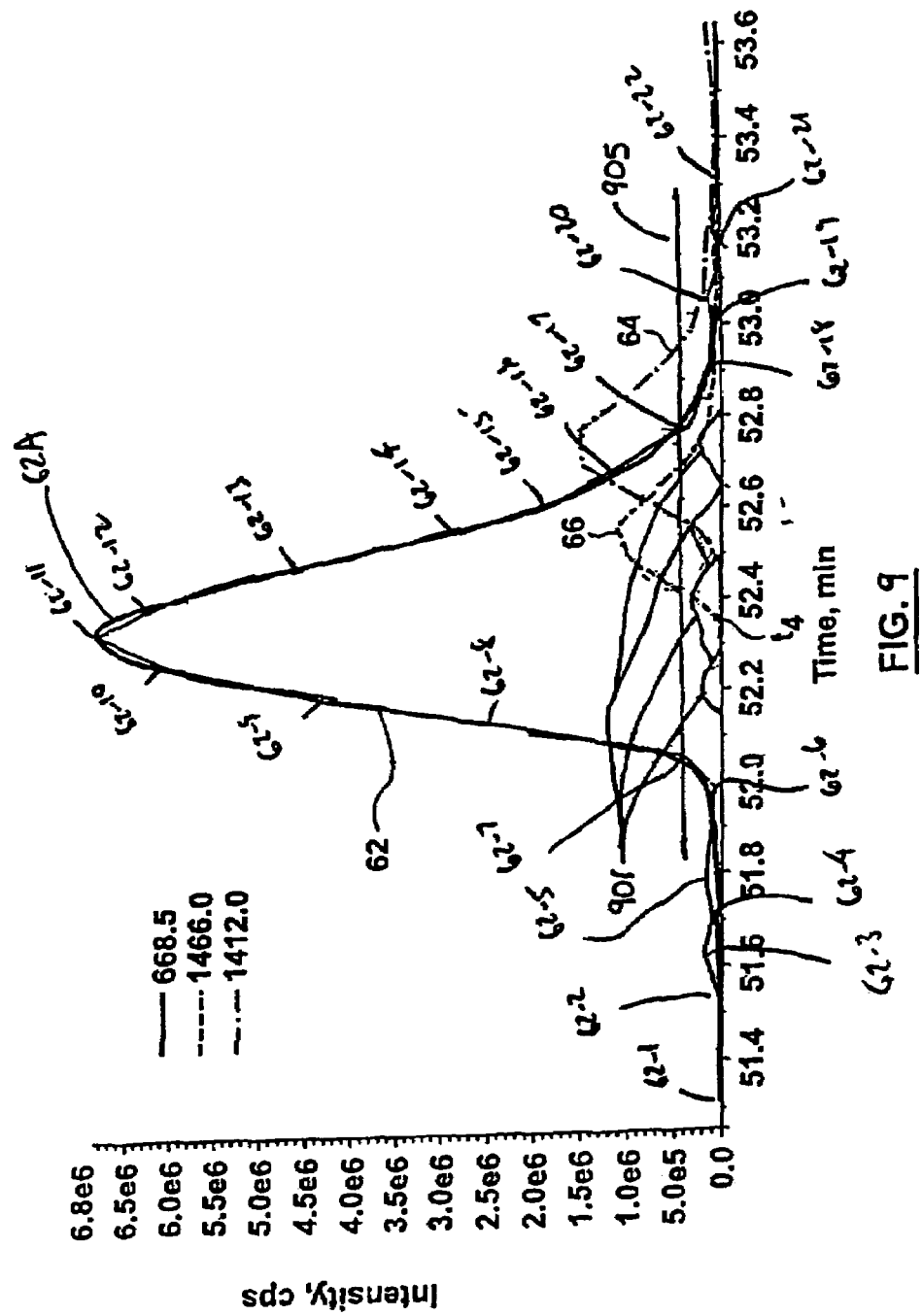
FIG. 9 is a diagram of an extracted ion chromatogram generated in accordance with the invention.

FIG. 9 includes a diagram of an XIC generated in accordance with this aspect of the invention. As previously described, curve 62 represents a first-order or straight line approximation generated by controller 16 using data provided by mass spectrometer 14 during 22 distinct survey scans, at times $t_1$-$t_{22}$. Using data representing intensities of ions of m/z of approximately 668.5 during the 22 recorded survey scans, controller 16 has generated and caused to be plotted or otherwise displayed data describing a curve 62A representing a smoothed XIC curve which probably more realistically approximates the actual elution of ions of that m/z ratio.

At 812 controller 16 can access data representing the smoothed XIC curve, e.g., curve 62A, and determine a first derivative or other value or function associated with a point of interest on the XIC, for use in determining, for example, at 814 whether XIC qualifies at the selected point as a fast-rising signal or whether the ion associated with the XIC otherwise qualifies for identification as an ion of interest, for inclusion in the peak list generated or applied at 804. For example, as previously described a user of system 10 can instruct controller 16 to identify one or more elutes or other ions provided by source 12 associated with fast-rising signals to be included in the peak list.

A current list of ions of interest being identified and, as appropriate, modified at 814, controller 16 can cause the list to be maintained in volatile or persistent memory, along with data defining one or more XICs of interest, and process 800 can be repeated with a second or subsequent MS survey at 802. The loop 802-814 can be repeated until all compounds of interest, or all relative proportions of interest, have been identified, or until controller 16 and/or a user of the system 10 is satisfied that a desired mass analysis is complete.

The invention improves the detection of low-intensity species co-eluting or otherwise provided by a source 12 in the presence of more concentrated species typically detected with high intensity. Consequently, it is expected that isotope and isotope ratio integrity may be preserved using this approach. In addition, the invention offers the possibility of simplifying the number of criteria that a user needs to enter in order to program the controller.

The invention also improves the efficiency in collection of useful information while minimizing the quantity of data collected. This offers for example the added benefits of minimizing the amount of information that has to be sifted through, and improving the real-time analysis capabilities for such data.

Preferred embodiments have been described with reference to scans which monitor single reactions. It will be understood, however, that the invention can be applied to a wide variety of further analysis processes, including for example selected ion monitoring (SIM), selected reaction monitoring (SRM), multiple reaction monitoring (MRM) (including where multiple generations of ion transformations are monitored) and multiple charged scans, as known in the art per se. It will also be understood that the invention can be applied to capillary electrophoresis mass spectrometry systems (CE-MS) and gas chromatography mass spectrometry systems (GC-MS). Those skilled in the art will appreciate that a variety of modifications may be made to the preferred embodiments without departing from the spirit of the invention.

FIG. 10, including parts 10a and 10b, provides tables of results, comparing analyses obtained in accordance with the present invention and according to regular IDA processes.

FIG. 10a represents analysis results for haloperidole metabolites detected and confirmed from single LC injections using conventional IDA features ("Regular-IDA") and using embodiments of systems and processes according to the invention ("IDA-DBS"). As noted in the table, significant improvement in success rate is obtained by using systems and processes according to the invention.

FIG. 10b represents analysis results for diclofenac metabolites detected and confirmed from single LC injections using conventional IDA features ("Regular-IDA") and using embodiments of systems and processes according to the invention ("IDA-DBS"). As noted in the table, significant improvement in success rate is obtained by using systems and processes according to the invention.

Figure 11:
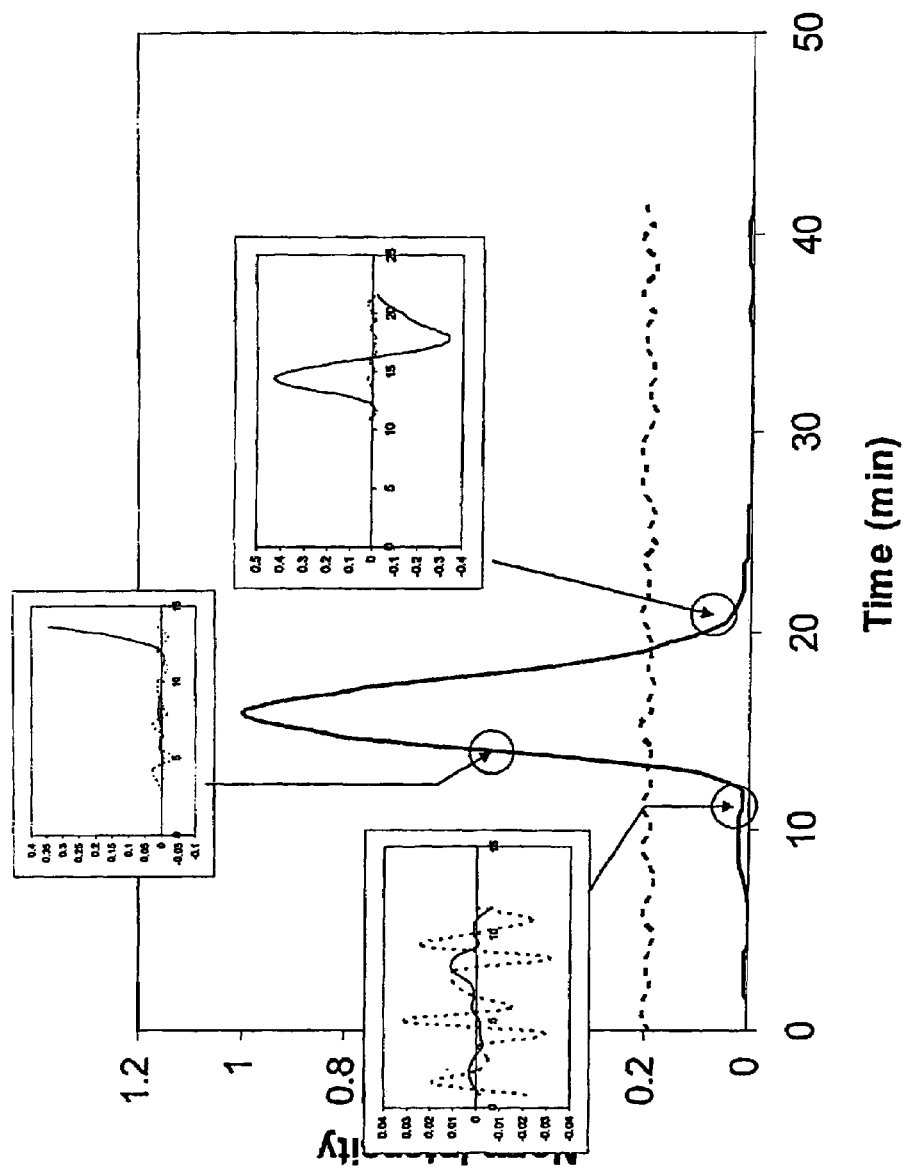
FIG. 11 is a plot of sample intensity (cps) of various masses detected as function of time (minutes) over a portion of an LC/MS run, with inset diagrams of local plot derivates.

FIG. 11 is a plot of sample intensity (cps) of various masses detected as function of time (minutes) over a portion of an LC/MS run, with inset diagrams of local plot derivates. Local derivatives such as those shown in the inset figures can be calculated using, for example, a desired number of past points in traces. In the example shown, two traces are presented, an LC peak for a selected ion in solid line and a flat signal in broken line. First derivative curves are shown for each of the traces, based on the last 20 data points provided by controller 16 and using curve-approximation algorithms as described herein. As the first derivative reaches its maximum value, at approximately 13.5 seconds (as shown in the middle inset figure), controller 16 causes the ion (or m/z ratio) associated with the solid line trace to be selected for further mass analysis.

While the foregoing invention has been described in some detail for purposes of clarity and understanding, it will be appreciated by one skilled in the art, from a reading of the disclosure, that various changes in form and detail can be made without departing from the true scope of the invention in the appended claims. The invention is therefore not to be limited to the exact components or details of methodology or construction set forth above. Except to the extent necessary or inherent in the processes themselves, no particular order to steps or stages of methods or processes described in this disclosure, including the Figures, is intended or implied. In many cases the order of process steps may be varied without changing the purpose, effect, or import of the methods described.

The invention claimed is:

1. A method of obtaining mass spectrographic data describing a substance, comprising:
   ionizing the substance;
   obtaining a current mass spectrogram of a portion of the ionized substance, and retaining data representing the current mass spectrogram;
   obtaining subsequent mass spectrograms of at least two further portions of the ionized substance, and retaining data representing the at least two subsequent mass spectrograms;
   generating information useful for describing at least one extracted ion chromatogram, using data associated with the current and at least two subsequent mass spectrograms and a non-linear curve approximation algorithm;
   using the generated information useful for describing at least one extracted ion chromatogram to generate further information useful in further analysis of the ionized substance.

2. The method of claim 1, wherein the generated information useful for describing at least one extracted ion chromatogram is used to generate information describing a derivative associated with the extracted ion chromatogram.

3. The method of claim 2, wherein the derivative associated with the extracted ion chromatogram is used to identify at least one ion associated with a fast-rising signal.

4. The method of claim 1, including conducting a precursor scan prior to obtaining a current mass spectrogram of a portion of the ionized substance.

5. The method of claim 1, including conducting a neutral loss scan prior to obtaining a current mass spectrogram of a portion of the ionized substance.

6. The method of claim 1, including comparing data representing at least one mass spectrum to data stored in a database representing a plurality of previously-determined mass spectrums in order to automatically identify a substance.

7. The method of claim 1, including reducing an amount of retained data representing at least one mass spectrogram by comparing data associated with at least one mass spectrogram to designated criteria, and retaining only data satisfying the criteria.

8. The method of claim 7, wherein the designated criteria include an intensity threshold.

9. The method of claim 7, wherein the designated criteria specify at least one ion of interest.

10. The method of claim 7, wherein the designated criteria specify at least one ion not of interest.

11. A mass spectrometer system, comprising:
    an ion source;
    a mass spectrometer capable of analyzing at least one ion of selected mass; and
    a controller adapted to:
      receive from the mass spectrometer and retain signals representing data representing a plurality of mass spectrograms;
      generate information useful for describing at least one extracted ion chromatogram, using data associated with the plurality of mass spectrograms and a non-linear curve approximation algorithm;
      use the generated information to generate further information useful in further analysis of the ionized substance.

12. The system of claim 11, wherein the controller is adapted to use the generated information useful for describing at least one extracted ion chromatogram to generate information describing a derivative associated with the extracted ion chromatogram.

13. The system of claim 12, wherein the controller is adapted to use the derivative associated with the extracted ion chromatogram to identify at least one ion associated with a fast-rising signal.

14. The system of claim 11, wherein the controller is adapted to compare data representing at least one mass spectrum to data stored in a database representing a plurality of previously-determined mass spectrums in order to automatically identify a substance.

15. The system of claim 11, wherein the controller is adapted to reduce an amount of retained data by comparing data represented by signals received from the mass spectrometer to designated criteria and retaining only data satisfying the criteria.

16. The system of claim 15, wherein the designated criteria include an intensity threshold.

17. The system of claim 15, wherein the designated criteria specify at least one ion of interest.

18. The system of claim 15, wherein the designated criteria specify at least one ion not of interest.

19. A controller for a mass spectrometer comprising a detector capable of detecting at least one ion of selected mass, the controller adapted to:
    receive from the mass spectrometer and retain signals representing data representing a plurality of mass spectrograms;
    generate information useful for describing at least one extracted ion chromatogram, using data associated with the plurality of mass spectrograms and a non-linear curve approximation algorithm;
    use the generated information to generate further information useful in further analysis of the ionized substance.

20. The controller of claim 19, adapted to use the generated information useful for describing at least one extracted ion chromatogram to generate information describing a derivative associated with the extracted ion chromatogram.

21. The controller of claim 20, adapted to use the derivative associated with the extracted ion chromatogram to identify at least one ion associated with a fast-rising signal.

22. The controller of claim 19, adapted to compare data representing at least one mass spectrum to data stored in a database representing a plurality of previously-determined mass spectrums in order to automatically identify a substance.

23. The controller of claim 19, adapted to reduce an amount of retained data by comparing data represented by signals received from the mass spectrometer to designated criteria and retaining only data satisfying the criteria.

24. A computer usable medium having computer readable code embodied therein for causing a controller of a mass spectrometer to:
- receive from a mass spectrometer and retain signals representing data representing a plurality of mass spectrograms;
- generate information useful for describing at least one extracted ion chromatogram, using data associated with the plurality of mass spectrograms and a non-linear curve approximation algorithm;
- use the generated information to generate further information useful in further analysis of the ionized substance.

25. The computer useable medium of claim 24, comprising computer readable code embodied therein to cause the controller to use the generated information useful for describing at least one extracted ion chromatogram to generate information describing a derivative associated with the extracted ion chromatogram.

26. The computer useable medium of claim 25, comprising computer readable code embodied therein to cause the controller to use the derivative associated with the extracted ion chromatogram to identify at least one ion associated with a fast-rising signal.

27. The computer useable medium of claim 24, comprising computer readable code embodied therein to cause the controller to compare data representing at least one mass spectrum to data stored in a database representing a plurality of previously-determined mass spectrums in order to automatically identify a substance.

28. The computer useable medium of claim 24, comprising computer readable code embodied therein to cause the controller to reduce an amount of retained data by comparing data represented by signals received from the mass spectrometer to designated criteria and retaining only data satisfying the criteria.

29. The computer useable medium of claim 28, wherein the designated criteria include an intensity threshold.

30. The computer useable medium of claim 28, wherein the designated criteria specify at least one ion of interest.

31. The computer useable medium of claim 28, wherein the designated criteria specify at least one ion not of interest.

* * * * *